(12) United States Patent
Wuebbeling et al.

(10) Patent No.: US 8,740,875 B2
(45) Date of Patent: Jun. 3, 2014

(54) METHOD OF JOINING TUBING FOR USE IN MEDICAL CATHETERS

(75) Inventors: Martin Wuebbeling, Mannheim (DE); Daniel Dietrich, Karlsruhe (DE)

(73) Assignee: C. R. Bard, Inc., Murray Hill, NJ (US)

( * ) Notice: Subject to any disclaimer, the term of this patent is extended or adjusted under 35 U.S.C. 154(b) by 89 days.

(21) Appl. No.: 13/386,291

(22) PCT Filed: Jul. 21, 2010

(86) PCT No.: PCT/EP2010/060560
§ 371 (c)(1),
(2), (4) Date: Jan. 20, 2012

(87) PCT Pub. No.: WO2011/009885
PCT Pub. Date: Jan. 27, 2011

(65) Prior Publication Data
US 2012/0289937 A1 Nov. 15, 2012

Related U.S. Application Data

(60) Provisional application No. 61/228,122, filed on Jul. 23, 2009.

(30) Foreign Application Priority Data

Jul. 23, 2009 (GB) .................................. 0912852.1

(51) Int. Cl.
*A61M 25/00* (2006.01)
(52) U.S. Cl.
USPC ............ 604/525; 604/523; 604/524; 604/526
(58) Field of Classification Search
USPC ........... 604/525, 19, 264, 523, 524, 526, 528, 604/530–532
See application file for complete search history.

(56) References Cited

U.S. PATENT DOCUMENTS

| 6,860,487 B2 | 3/2005 | Shiokawa et al. |
| 2003/0191492 A1* | 10/2003 | Gellman et al. ............... 606/200 |
| 2007/0244550 A1* | 10/2007 | Eidenschink ................ 623/1.49 |

FOREIGN PATENT DOCUMENTS

| EP | 0856331 A2 | 8/1998 |
| EP | 1050317 A1 | 11/2000 |
| WO | 2007100365 A1 | 9/2007 |

OTHER PUBLICATIONS

PCT/EP2010/060560 filed Jul. 21, 2010 International Preliminary Report on Patentabillity dated Jun. 29, 2011.
PCT/EP2010/060560 filed Jul. 21, 2010 International Search Report dated Oct. 14, 2010.
PCT/EP2010/060560 filed Jul. 21, 2010 Written Opinion dated Oct. 14, 2010.

* cited by examiner

*Primary Examiner* — Aarti B Berdichevsky
*Assistant Examiner* — Niyati D Shah
(74) *Attorney, Agent, or Firm* — Rutan & Tucker, LLP

(57) ABSTRACT

The present application relates to method of arresting telescopic endwise relative movement in a medical device between an end portion of an elongate member, preferably being a cylinder, and an end portion of a tube, preferably being a cylindrical tube, that receives the end portion of the elongate member. The method is of particular use in the construction of stent delivery systems. In one embodiment, the method comprises providing a length of deformable blocking material; imparting relative endwise movement to draw the blocking material, into the gap and reversing the direction until the blocking material length suffers deformation.

18 Claims, 4 Drawing Sheets

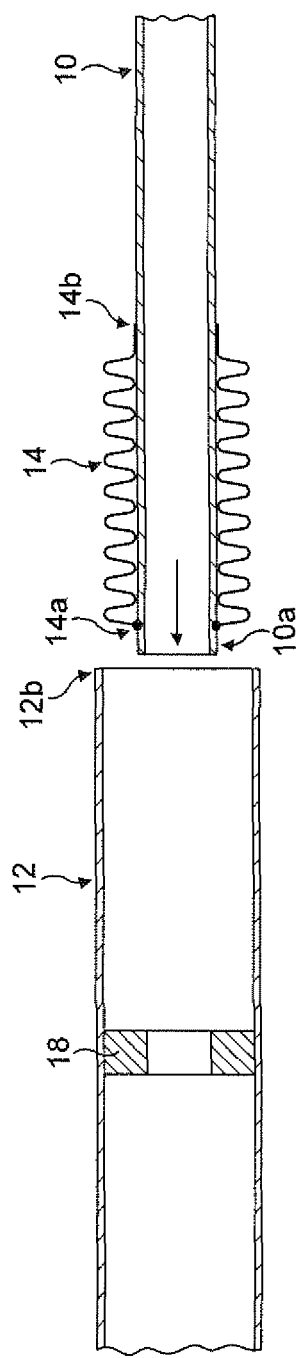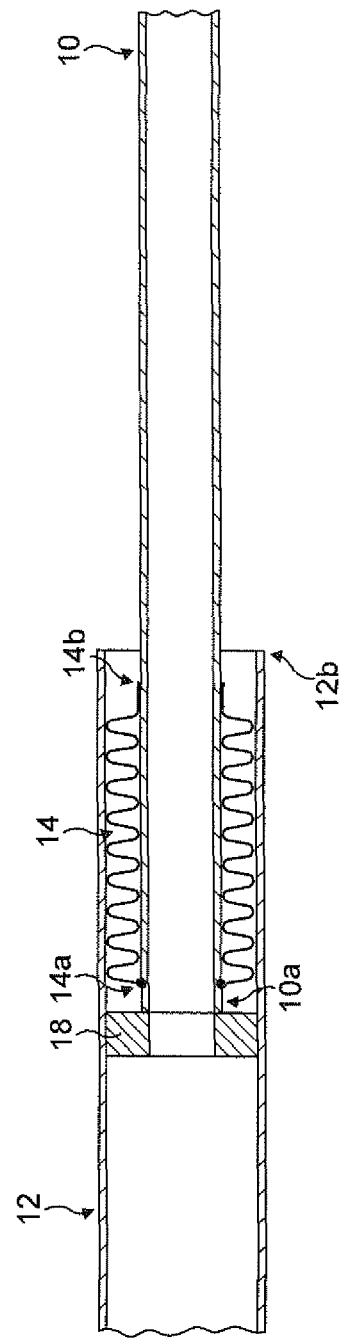

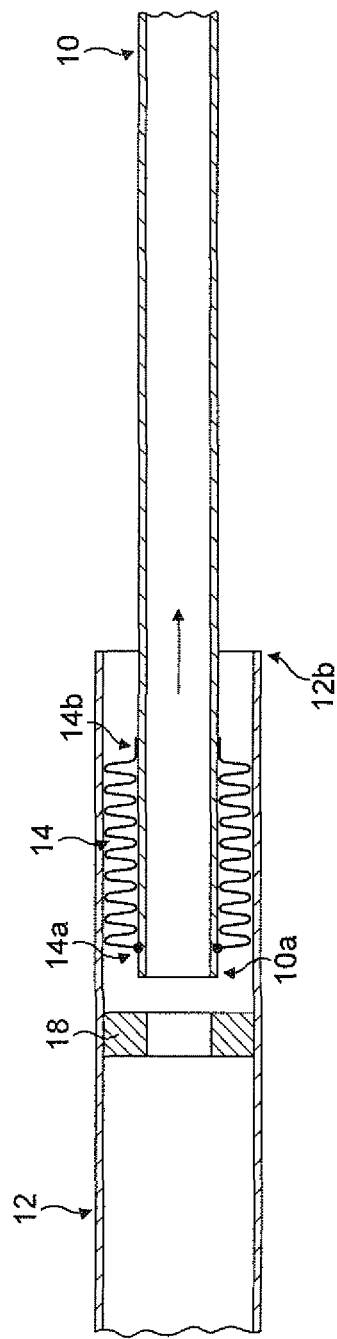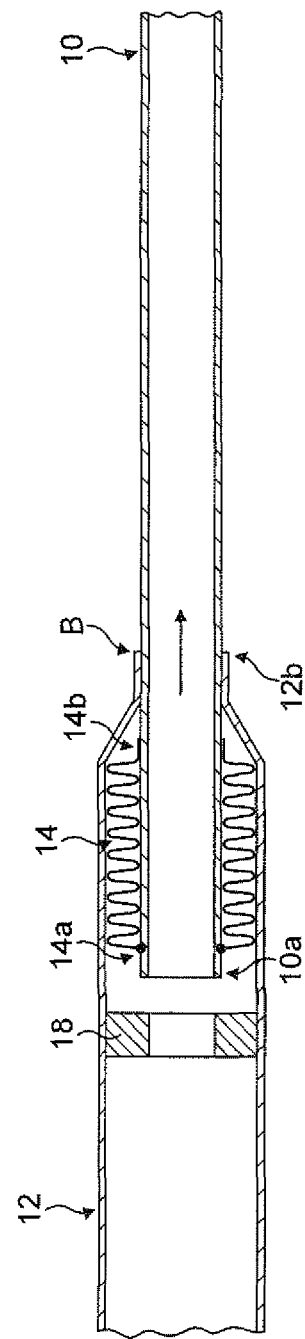

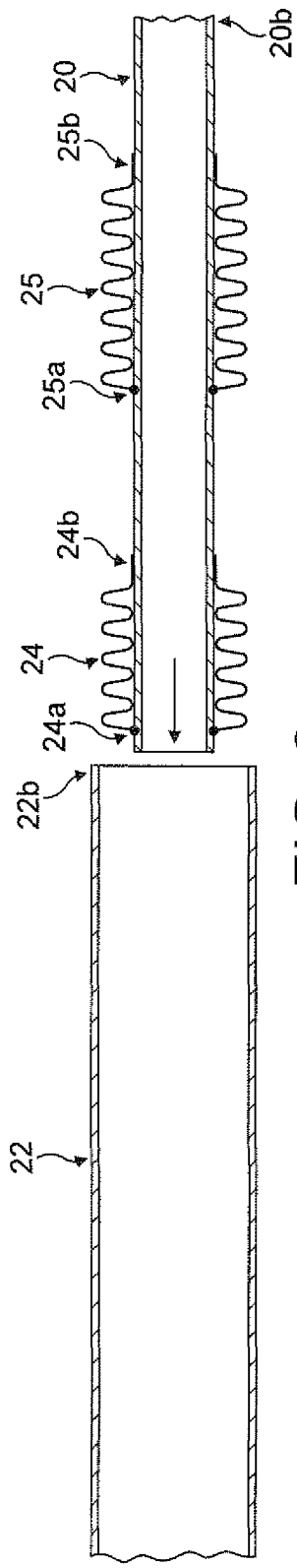
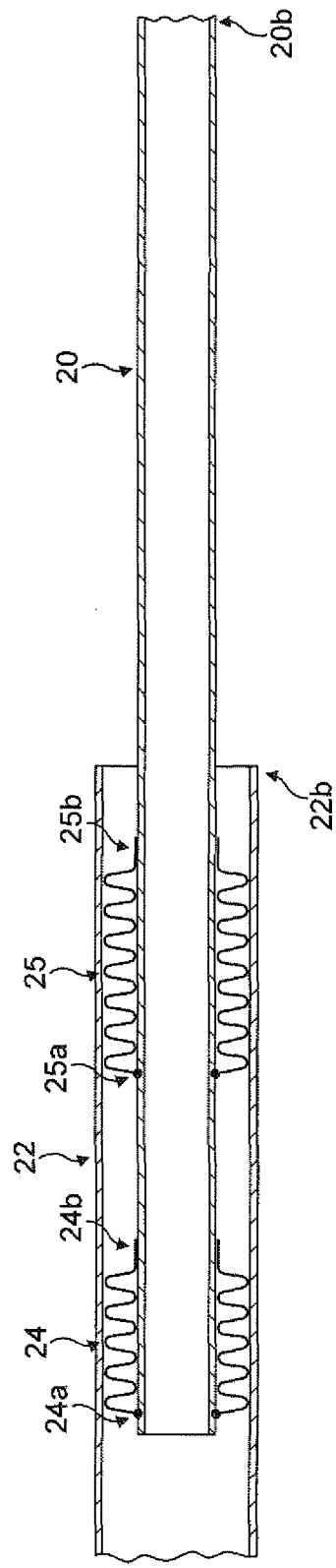
FIG. 2a
FIG. 2b

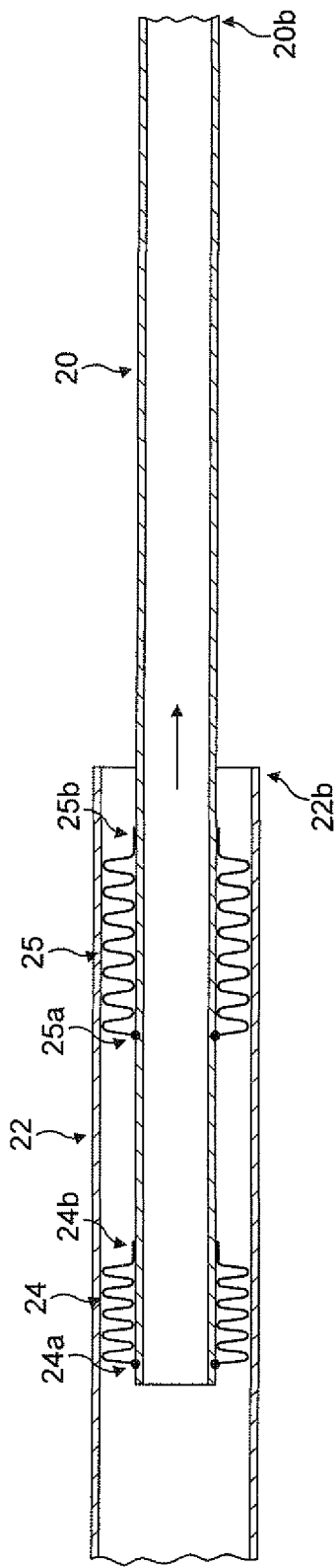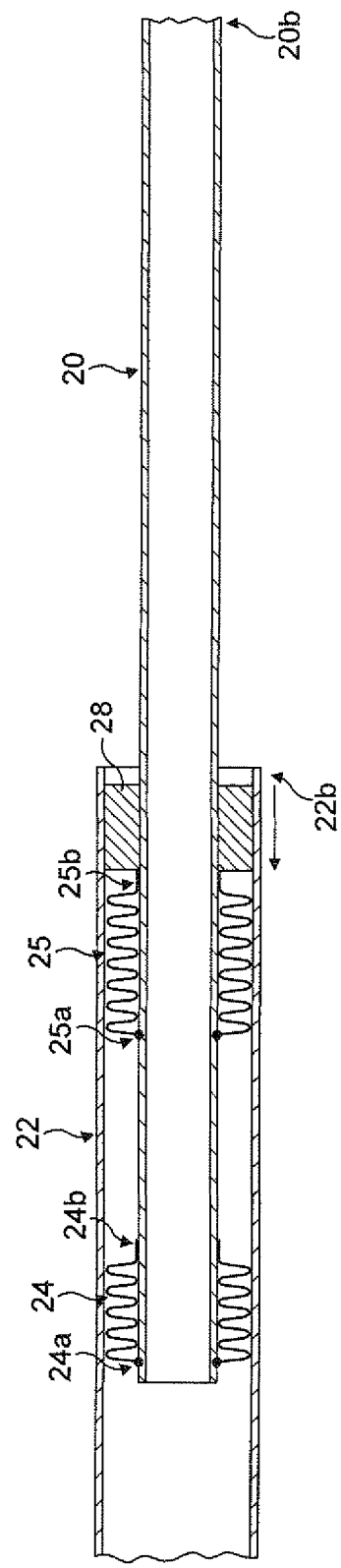

METHOD OF JOINING TUBING FOR USE IN MEDICAL CATHETERS

PRIORITY

This application is a U.S. national stage application under 35 U.S.C. §371 of International Application No. PCT/EP2010/060560, filed Jul. 21, 2010, claiming priority to United Kingdom Patent Application No. 0912852.1, filed Jul. 23, 2009, and to U.S. Provisional Application No. 61/228,122, filed Jul. 23, 2009, each of which is incorporated by reference in its entirety into this application.

FIELD OF THE INVENTION

The present invention relates to a method of forming a joint between at a tube and an elongate member, preferably being a cylinder, and particularly to forming a joined tube suitable for use in the manufacture of medical catheters. The present invention also relates to a joint so formed.

BACKGROUND ART

In diverse fields of engineering, there exists a requirement to engage two tubular members in permanent or semi-permanent relation. Welding, glueing, swaging and brazing are all known techniques for attaching tubes. However, each of these techniques is subject to a failure threshold; as the strain on the joint increases, the probability of failure increases, and having failed, the joint requires a repetition of the joining process to reform. Such failure may be detrimental or dangerous in the context of the application of the joint, and repair may be difficult.

One field in which the failure of welded, swaged or glued joints is particularly disadvantageous is in the construction of medical devices, particularly catheters. Catheters are tubular structures which are navigated through body cavities to perform some diagnostic or therapeutic function at a specific location within the body. If a joint in a catheter fails, there is risk not only of failure of the process for which the catheter is used but also of further risks due to the presence of a structurally compromised and thus unpredictable foreign body inside a patient's body. The presence of such risks restricts the use of catheterization techniques to cases where the risks can be justified.

Accordingly, there is a need for a method of forming a joint between at least two tubular catheter elements which is able to resist such sudden failure modes.

SUMMARY OF THE INVENTION

According to a first aspect of the present invention, there is provided a method of arresting telescopic endwise relative movement in a medical device between an end portion of an elongate member, preferably being a cylinder, and an end portion of a tube, preferably being a cylindrical tube, that receives the end portion of the elongate member, the method comprising the steps of: providing a length of deformable blocking material; attaching a leading end of the length to either the radially outer surface of the elongate member or the inner surface of the tube; imparting such relative endwise movement to the elongate member and the tube as will draw the leading end of the blocking material, followed by its length, into the gap, which may preferably be an annular gap, between the elongate member and the tube; and reversing the direction of relative endwise movement and continuing until the blocking material length suffers such endwise deformation as to defeat any further such reverse endwise movement.

According to a second aspect of the present invention, there is provided a method of forming a joint in a medical device between at least a tube, preferably being a cylindrical tube, and an elongate member, preferably being a cylinder, comprising the steps of placing a first section of a tubular sleeve material at least partially surrounding a portion of the elongate member; fixing the sleeve to the elongate member at a distal end of the sleeve; inserting in a distal direction the portion of the elongate member surrounded by the sleeve into the tube; and applying tensile force in a proximal direction to the elongate member relative to the tube such that the sleeve changes configuration to apply increased friction to at least the inner surface of the tube.

According to a variant of the second aspect of the present invention, there is provided a method of forming a joint in a medical device between an elongate member, preferably being a cylinder, and a tube, preferably being a cylindrical tube, comprising the steps of placing a first section of a tubular sleeve material inside a portion of a tube; fixing the sleeve to the tube at a proximal end of the sleeve; inserting in a distal direction a portion of the elongate member into the tube so as to pass the sleeve; and applying tensile force in a proximal direction to the elongate member relative to the tube such that the sleeve changes configuration to apply increased friction to at least the outer surface of the elongate member.

In such joined tubes, applied tensile forces tend to increase friction further between the sleeve and the elongate member and the tube, respectively. Thus the joint is less, rather than more, likely to fail under increased tensile force.

Further, the success of the joint formation may be tested shortly after assembly by application of a relatively small tensile force, as the joint will tend to strengthen, not weaken, under increased tensile force.

It is also important to note that such a construction is able to provide a joint having a reduced profile than that achievable with conventional techniques such as glueing.

In some embodiments of the present invention, the sleeve material or blocking material is formed from a material that crumples or folds to provide the increased friction.

In other embodiments of the first aspect of the present invention, the sleeve material or blocking material is formed from a resilient material that deforms under compression to provide the increased friction.

In presently preferred embodiments of the first aspect of the present invention, the sleeve material or blocking material is formed from a tubular braided material which expands radially under endwise compression to provide the increased friction.

Such a construction allows the components to be joined with the minimum of manufacturing complexity. Such a construction also permits the joining of components that might otherwise be incompatible in or damaged by conventional joining techniques, such as gluing, swaging, fusing or welding.

In some embodiments of the invention, the tube is fixed to the elongate member proximal of the sleeve material or blocking material.

Such a construction is useful for improving the integrity of the joint to ensure that the joint is sufficiently fluid-sealed.

Preferred embodiments of second aspect of the invention comprise, prior to the step of placing the elongate member inside the tube, a step of placing a second section of sleeve surrounding a portion of an elongate member proximal of the first section of sleeve; a step of fixing the second section of sleeve to the elongate member at a distal end of the sleeve; and subsequent to the step of applying tensile force in a proximal direction to the elongate member relative to the tube, a step of translating the proximal end of the second section of sleeve toward the distal end of the tube such that the second section of sleeve changes configuration to apply increased friction to the radial space between the elongate member and the tube.

Such a construction allows the joint to have increased resistance to compressive forces as well as resistance to tensile forces.

In further preferred embodiments of the second aspect of the invention, the second section of sleeve is longer than the first section of sleeve.

Such a construction allows the joint to have a balanced resistance between compressive forces and tensile forces.

In further preferred embodiments of the second aspect of the invention, the step of translating the proximal end of the second section of sleeve toward the distal end of the second tube is accomplished by means of application of an annular plug to the proximal end of the second section of sleeve.

Such a construction is convenient for manufacture and permits a smooth transition across the junction between the outer surfaces of the two tubes.

In accordance with a third aspect of the invention, there is provided a joined tube produced by any of the above-described methods.

Such a joined tube has improved tolerance to failure under tensile force.

In accordance with a fourth aspect of the invention, there is provided a tube joint comprising at least an elongate member, preferably being a cylinder, and a tube, preferably being a cylindrical tube, having a first section of a tubular sleeve material at least partially surrounding a portion of the elongate member and fixed to the elongate member at a distal end of the sleeve; the portion of the elongate member surrounded by the sleeve being located inside the tube; wherein under tensile force the sleeve is arranged to change or has changed configuration to apply increased friction to at least the inner surface of the tube.

Such a tube joint also provides improved tolerance to failure under tensile force.

In embodiments wherein the tube and/or the elongate member are cylindrical or substantially cylindrical, relative axial rotational orientation between the tube and the elongate member need not be brought into specific alignment prior to assembly.

In all the foregoing, the elongate member may be fully or partially hollow, and may form another tube. Tubes used in the present invention may be open at both ends or closed at one or both ends.

BRIEF DESCRIPTION OF THE ACCOMPANYING DRAWINGS

To better understand the present invention, and to show how the same may be carried into effect, reference will be made, by way of example only, to the accompanying Drawings, in which:

FIG. 1(*a* to *d*) show a first embodiment of the method of the present invention; and FIG. 2(*a* to *d*) show a second embodiment of the method of the present invention.

DETAILED DESCRIPTION OF THE INVENTION (BEST MODE)

An embodiment of the method of the first aspect of the present invention is shown in FIG. 1(*a*) to FIG. 1(*d*).

In FIG. 1(*a*) we see two polymer tubes. The first tube 10 has outer diameter 1 mm, while the second tube 12 has inner diameter 1.2 mm. Such values are exemplary, as the diameter of the tubes will be selected on the basis of the use to which the tube will be put. Here, the tubes each have wall thickness 0.1 mm, and are formed of polyamide.

Both tubes are substantially cylindrical in cross-section; this naturally need not be the case, and minor and/or major deviations from a cylindrical cross-section are contemplated that would enable the invention to be put into effect, as the skilled reader will understand from the disclosure herein. Both tubes are here also open for fluid passage at each end thereof; this, however, need not be the case to put the invention into effect.

Around the first tube 10 is positioned a section of sleeve 14, in the present case having inner diameter 1 mm and outer diameter 1.2 mm. Accordingly, the sleeve fits reasonably snugly about the first tube. The sleeve may, for example, be metallic braid. In the present embodiment it is a tubular braid formed from stainless steel fibers. The fibers are of SS304W stainless steel, 0.01 mm in cross-section and braided at 100 PPI (crossing points per inch). Sixteen wire bands are used in the braid. It is fixed, at its distal end 14*a*, to the first tube. Most preferred is a method of construction in which the metallic braid is secured with a ring of heat-shrink tubing placed about its distal end 14*a*, which ring is subsequently heat-shrunk to compress the distal end 14*a* of the metallic tubing against the outer surface of the first tube. Other embodiments of the invention may use other methods for fixing the sleeve to the first tube, such as gluing with, for example, cyanoacrylate adhesive, swaging or welding.

In any case, the strength of the fixing of the sleeve relative to the first tube need not be high, as the joint will eventually be secured by the direct interaction between the braiding and the first and second tubes, rather than by virtue of the fixing technique used.

A proximal end 12*b* of the second polymeric tube 12 is located coaxial with and distal of the distal end 10*a* of the first polymeric tube 10. The second polymeric tube has an inner diameter suitable to accommodate within it the first polymeric tube having the section of sleeve fixed thereon.

The dimensions of the sleeve 14 are selected to ensure a close fit into the annular void formed between the first and second tubes when the tubes are placed concentrically one within the other.

In FIG. 1(*b*) we see the first 10 and second 12 tubes now with the portion of the first tube having the sleeve 14 thereon located entirely inside a proximal end portion of the second tube. The proximal end 14*b* of the sleeve is not fixed to the second tube, and thus the first tube may be further inserted distally further into the second tube. Especially in the case of the sleeve fitting very closely within the second tube, the friction between the inner surface of the second tube and the sleeve will tend to elongate the sleeve, reducing its outside diameter and permitting the first tube to slide freely within the second tube. An annular internal stop 18 may be provided to the second tube to prevent the first tube from being inserted too far into the second tube.

However, when longitudinal tensile force may now be applied to the first 10 and second 12 tubes, the sleeve 14 changes configuration to the state shown in FIG. 1(*c*), and thereby applies increased friction to at least the inner surface of the second tube.

In general, it is preferable that the sleeve is arranged such that it applies increased friction also to the outer surface of the first tube, to strengthen the joint. In the present embodiment, using a tubular braid, the braid applies friction to both surfaces when under lengthwise compression.

Forces applied to the tubes are borne directly by the interaction between the sleeve and the two tubes. The joint is complete.

In the case of the present embodiment, in which the sleeve is a braided tube, the increased friction is engendered by the radial expansion of the braided tube under longitudinal compression. Braids are particularly useful as the filaments of the braid tend to bite into the material of the second tube, improving the strength of the joint.

However, other methods of realising this joint are also contemplated in the present invention.

For example, a resilient tube which snugly fits into the annular void between the first and second tube will, due to frictional interaction with the inner surface of the second tube, tend to longitudinally compress under longitudinal tensile force between the tubes. In doing so, it will expand radially, increasing the frictional interaction.

Alternatively, a material which has some degree of freedom to move within the annular void, for example a polymer film which may be crushed, crumpled or concertina-ed within the annular void will, under compression, tend to crumple to form a packed plug of material which will apply increased friction to at least the inner surface of the second tube and preferably increased friction between the tubes. The sleeve need not be entirely circumferentially contiguous: a band of material from which streamers of material proximally extend will, on proximal movement within a tube, tend to chaotically crumple to form a packed plug.

It is also possible to realise the joint with multiple sections of sleeve similarly configured, so as to provide increased resilience and redundancy of join.

The skilled person can undoubtedly imagine other related configurations which will realise the invention. For example, in the above embodiment, the tubes and sleeve lie substantially concentric to one another. However, in some embodiments, the sleeve material need not entirely enclose the first tube, but may lie to one side thereof, or the tubes and sleeve may have noncircular or asymmetric cross-sections. Provided that the sleeve engenders increased friction under tensile force or relative motion between the two tubes, the joint geometry can be varied to suit the application.

To improve the stability of the join, the proximal end 12b of the second tube 12 may be attached to the outer surface of the first tube, as shown in FIG. 1(d), in the present embodiment by welding (at point B). Adhesion or other fixing techniques may equivalently be used. Such a construction can provide an improved fluid-sealed join to allow the joined tubes to transport liquid along their lengths. However, in cases where the sleeve is sufficiently long, the sleeve material, such as braid, can provide a labyrinth seal to impede leakage of fluid through the joint. The skilled person will find it well within his ability to determine the correct length of sleeve required to withstand particular fluid pressures and viscosities.

In FIG. 2(a) to FIG. 2(d), a second embodiment of the method of the first aspect of the present invention is shown.

FIG. 2(a) shows a similar initial structure to FIG. 1(a), except that there are two sections of sleeve, a first section 24, with proximal end 24b, and a second section 25, with proximal end 25b, positioned around and concentric with the first tube 20. For convenience of reference, the first section 24 is taken to be distal of the second section 25. Both sections of sleeve are fixed, at their distal ends 24a and 25a, to the first tube with the use of cyanoacrylate adhesive. Again, other conventional fixing techniques may be used. In the present embodiment, the second section of sleeve is longer than the first section of sleeve. The sleeve is otherwise identical to that of the embodiment of FIG. 1(a).

In FIG. 2(b) we see the first 20 and second 22 tubes now with the portion of the first tube having the two sections of sleeve thereon located entirely inside a proximal end portion of the second tube. Longitudinal tensile force may now be applied to the first and second tubes.

Under tensile force, the first 24 and second 25 section of sleeve change configuration to the state shown in FIG. 2(c). Both sections of sleeve have changed configuration to apply increased friction to the inner surface of the second tube 22. As noted before, with respect to the first embodiment, it is preferable that the sleeve is arranged such that it applies increased friction also to the outer surface of the first tube, to strengthen the joint. In the present embodiment, using a tubular braid, the braid applies friction to both surfaces when under lengthwise compression.

However, due to the length of the second section relative to the first section, the radial force exerted on the inner surface of the second tube by the second section relative to that exerted by the first section is correspondingly less.

Accordingly, to arrive at the final joint shown in FIG. 2(d), an end plug 28 is pushed from a proximal end 20b of the first tube 20 to abut and compress the proximal end 22b of the second section of sleeve 25. In so doing, the degree of crumpling of the second section is increased and the radial force exerted on the first and second tubes in the region of the second section is correspondingly increased. The joint is now in a secured state which can resist both tensile and compressive force. Welding, gluing, press-fitting or other fixing techniques may equivalently be used to fix the plug in position. In the present embodiment, cyanoacrylate adhesive is used to fix the end plug 28 in position. Compression across the joint will tend to then press the end plug against the sleeve and will thus secure the joint against compressive, as well as tensile, force.

Again, as the joint is secured principally by the radial forces from the braided sections on the first and second tubes, the fixing technique applied to the end cap does not determine the strength of the joint.

Any of the above-mentioned embodiments can also be realized in a configuration in which, instead of the distal end of the section or sections of sleeve being fixed to the first tube, the proximal end of the section or sections of sleeve may be fixed to the inner surface of the second tube. To form the joint, the first tube is then inserted into the second tube so that it passes the sleeve or sleeves. As this construction is a complementary method to the above-mentioned construction, the same effects can occur. In particular, the application of tensile force across the joint will result in the sleeve being deformed, folded or compressed longitudinally and thus applying increased friction to at least the outer surface of the first tube.

Any of the embodiments mentioned above may be suitably used to join lengths of appropriately-constructed catheter tubing for medical applications. In other applications, the first (inner) tube may be replaced by a cylinder or rod, as the inner void (lumen) of the first tube plays no significant role in the joining process.

The present invention is not limited to the presently disclosed embodiments, but rather solely by the scope of the appended claims. The skilled reader will easily contemplate how embodiments of the method of joining tubes may be incorporated into other constructions where reliance on swaged, welded or glued joints, or the like, is undesirable. Such embodiments may not be herein explicitly described, but will nevertheless be clearly within the ambit of the skilled reader without undue experimentation and without the exercise of inventive skill.

The invention claimed is:

1. A method of arresting telescopic endwise relative movement in a medical device between an end portion of an elongate member and an end portion of a tube that receives the end portion of the elongate member, the method comprising the steps of:
   providing a length of deformable blocking sleeve material;
   attaching a leading end of the length to either an outer surface of the elongate member or an inner surface of the tube;
   imparting such relative endwise movement to the elongate member and the tube as will draw the leading end of the blocking sleeve material, followed by its length, into a gap between the elongate member and the tube; and
   reversing a direction of the relative endwise movement and continuing until the blocking sleeve material length suffers an endwise deformation so as to defeat any further reverse endwise movement,
   wherein the blocking sleeve material crumples or folds under the reversed relative endwise movement to provide increased friction.

2. The method of claim 1 wherein the elongate member is cylindrical.

3. The method of claim 1 wherein the tube is cylindrical.

4. A method of forming a joint in a medical device between the elongate member of claim 1 and the tube of claim 1 employing the method of claim 1, in which method:
   the sleeve material is a tubular sleeve material which has a first section that at least partially surrounds a portion of the elongate member;
   the sleeve is first fixed to the elongate member at a distal end of the sleeve;
   the portion of the elongate member surrounded by the sleeve is next inserted in a distal direction into the tube; and
   a tensile force is then applied in a proximal direction to the elongate member relative to the tube such that the sleeve changes configuration to apply increased friction to at least the inner surface of the tube.

5. The method of claim 4, wherein the tube is fixed to the elongate member proximal of the sleeve material.

6. The method of claim 4, further comprising, prior to the step of inserting the portion of the elongate member into the tube:
   placing a second section of sleeve surrounding a portion of the elongate member proximal of the first section of sleeve;
   fixing the second section of sleeve to the elongate member at a distal end of the sleeve; and
   subsequent to the step of applying tensile force in the proximal direction to the elongate member relative to the tube,
   translating a proximal end of the second section of sleeve toward a distal end of the tube such that the second section of the sleeve changes configuration to apply increased friction to a radial space between the elongate member and the tube.

7. The method of claim 6, wherein the second section of sleeve is longer than the first section of sleeve.

8. The method of claim 6, wherein the step of translating the proximal end of the second section of sleeve toward the distal end of the tube is accomplished by means of application of an annular plug to the proximal end of the tube.

9. The method of claim 4 wherein the elongate member is cylindrical.

10. The method of claim 4 wherein the tube is cylindrical.

11. A method of forming a joint in a medical device between the elongate member of claim 1 and the tube of claim 1 employing the method of claim 1, in which method:
   the sleeve material is a tubular sleeve material;
   the sleeve is first fixed inside a portion of the tube at a proximal end of the sleeve;
   a portion of the elongate member is next inserted in a distal direction into the tube so as to pass the sleeve; and
   a tensile force is then applied in a proximal direction to the elongate member relative to the tube such that the sleeve changes configuration to apply increased friction to at least the outer surface of the elongate member.

12. The method of claim 11, wherein the tube is fixed to the elongate member proximal of the sleeve material.

13. The method of claim 11 wherein the elongate member is cylindrical.

14. The method of claim 11 wherein the tube is cylindrical.

15. A joint in a medical device, comprising:
   at least an elongate member and a tube with a radial space between the elongate member and the tube and having a first section of a tubular sleeve material at least partially surrounding a portion of the elongate member and fixed to the elongate member at a distal end of the first section of sleeve;
   the portion of the elongate member surrounded by the first section of sleeve being located inside the tube; and
   a second section of sleeve surrounding a portion of the elongate member proximal of the first section of sleeve, fixed to the elongate member at a distal end of the sleeve;
   a proximal end of the second section of sleeve having been additionally compressed toward a distal end of the joint by means of an annular plug;
   wherein under tensile force across the joint, the first section of sleeve changes configuration to apply increased friction to at least an inner surface of the tube;
   wherein the first section of sleeve is formed from a material which crumples or folds to provide the increased friction
   wherein under the tensile force across the joint, the second section of the sleeve changes or has changed configuration to apply increased friction to the radial space between the elongate member and the tube, and
   wherein the second section of sleeve is formed from a material which crumples or folds, to provide the increased friction.

16. The joint of claim 15, wherein the tube is fixed to the elongate member proximal of the sleeve.

17. The joint of claim 15, wherein the second section of sleeve is longer than the first section of sleeve.

18. The method of claim 15 wherein the elongate member is cylindrical.

* * * * *